United States Patent [19]

Cross

[11] Patent Number: 4,494,380
[45] Date of Patent: Jan. 22, 1985

[54] THERMOELECTRIC COOLING DEVICE AND GAS ANALYZER

[75] Inventor: Ronald H. Cross, Hickory Corners, Mich.

[73] Assignee: Bilan, Inc., Kalamazoo, Mich.

[21] Appl. No.: 602,193

[22] Filed: Apr. 19, 1984

[51] Int. Cl.³ ............................................. F25B 21/02
[52] U.S. Cl. ....................................................... 62/3
[58] Field of Search ............................................. 62/3

[56] References Cited

U.S. PATENT DOCUMENTS 3,205,667 9/1965 Frantti ...................................... 62/3
3,255,593 6/1966 Newton ................................... 62/3

Primary Examiner—Lloyd L. King
Attorney, Agent, or Firm—Gordon W. Hueschen

[57] ABSTRACT

There is disclosed a thermoelectric device suitable for drying gases in which a finned heat-dissipating device is in contact with the hot face of a thermoelectric element and a thermal sink is in contact with the cold face thereof. The thermal sink has formed therein a conduit which zig-zags from an inlet at the upper part thereof to a point at the bottom thereof and then upwardly to an outlet at the other side. The conduit is formed by routing out a channel in a block and sealing it off with a face plate to provide the desired conduit. The various elements are held together by face plates spanning the heat-radiating device and the thermal sink, and the space between the two is desirably filled with insulating material. The device is used in combination with a gas analyzer in which exhaust gases, for example, from an internal combustion engine, are fed through the dryer and then into the analyzer.

12 Claims, 4 Drawing Figures

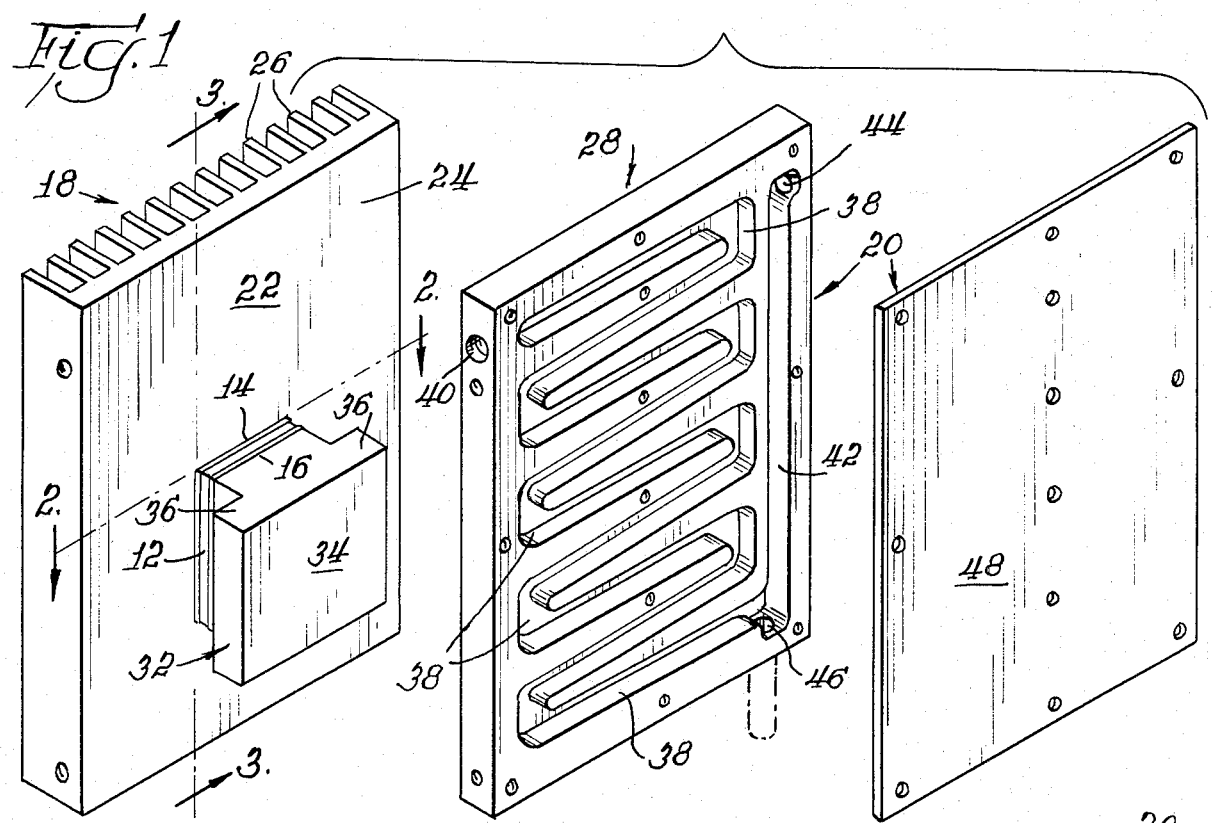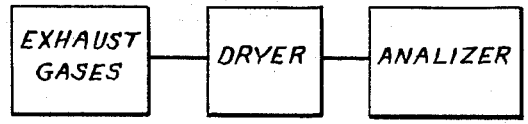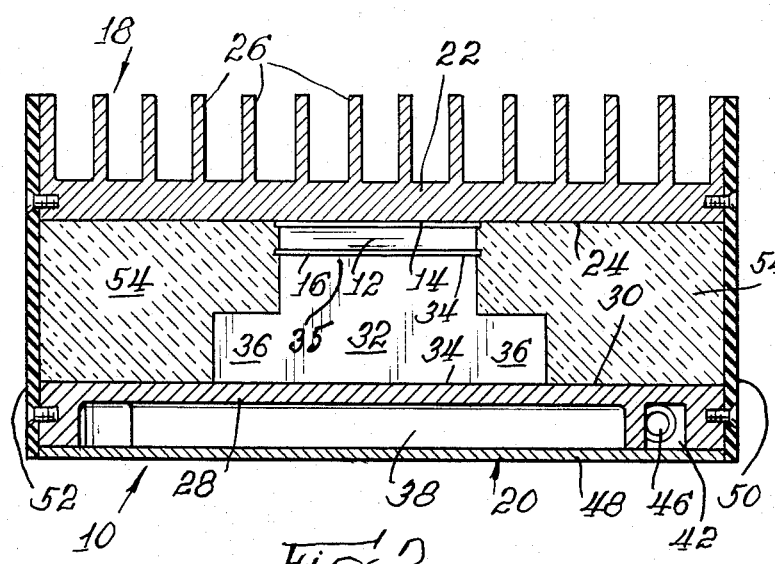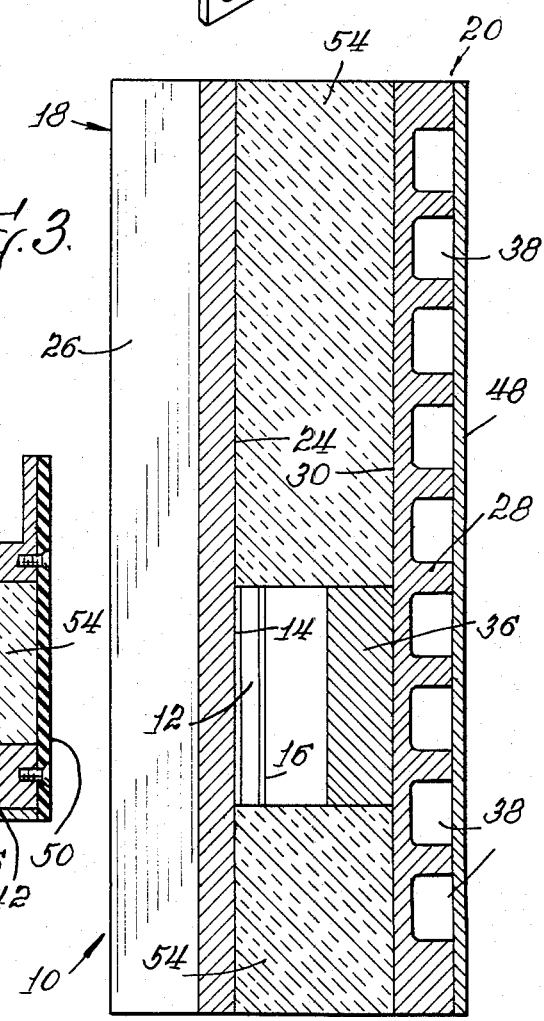

4,494,380

THERMOELECTRIC COOLING DEVICE AND GAS ANALYZER

BACKGROUND OF THE INVENTION

The invention relates to a thermoelectric cooling device and is particularly directed to a thermoelectric device useful for either drying gases or cooling liquids. Still more particularly, the invention lies in using the thermoelectric cooling device of the invention for drying exhaust gases, for example, the exhaust gases of an internal combustion engine, before feeding them into an analyzer.

FIELD OF INVENTION AND PRIOR ART

Thermoelectric elements in which one face becomes hot and the other becomes cold when a direct current potential is impressed across the two faces are well known in the art. One application of such thermoelectric elements is described in U.S. Pat. No. 3,212,274, wherein the cold face is utilized to effect condensation of a condensable gas in air conditioning and refrigeration and the like.

The condensers of the patent comprise a thermoelectric element having a heat-radiating device in contact with and coextensive in area with the hot face thereof and a thermal sink coextensive in area with and in heat contact with the cold face of the thermoelectric element. In one form of the invention, the thermal sink comprises a block of heat-conducting material having a condensing chamber taking the shape of a multi-curved, thermally-conductive hollow tube affixed to a flat surface of the thermal sink. Such a device has the disadvantage that it is not suitable for drying gas because the condenser tube zig-zags from one side to the other side so that, if the device were used for drying gas, there would be no separation of the gas and the liquid condensed therefrom.

Furthermore, the devices of this patent are inefficient because the heat-radiating devices and the thermal sinks have inadequate capacity to utilize fully the cooling potential of the thermoelectric element.

In many automotive shops nowadays, it is customary to analyze the exhaust gases of an internal combustion engine for diverse purposes, such as for determining the efficiency of omission controls and for determining the optimum conditions for operating the engine. Difficulty has been encountered, however, due to the moisture content of the exhaust gases interfering with the efficiency of the analyzer and the drying means or devices heretofore available have been so cumbersome and inefficient that they tend to complicate the problem rather than to solve it.

OBJECTS OF THE INVENTION

It is a particular object of the invention to provide a thermoelectric device effective for drying gases. It is a further object of the invention to provide a thermoelectric device of the character described which is relatively small and portable and which can be used to dry gases fed into analytical devices. It is a further object of the invention to provide a thermoelectric device of the class described which is simple and easily assembled. It is a further object of the invention to provide a thermoelectric device of the class described which is versatile in its applications and can be used, if desired, simply for cooling liquids. Still other objects are to avoid the disadvantages of the prior art and to obtain such advantages as will appear as the description proceeds.

SUMMARY OF THE INVENTION

The invention relates to a thermoelectric device comprising a thermoelectric element having a cold face and a hot face, a heat-radiating device in heat-transfer with said hot face and having a flat, inner surface having a substantially greater area than the area of contact with said hot face and a thermal sink in heat-transfer contact with said cold face and comprising a flat, inner surface apposed to the flat, inner surface of said heat-radiating device and having an area substantially coextensive with the area of the flat, inner surface of the heat-radiating device, and a conduit in heat-transfer with said thermal sink, said conduit zig-zagging back and forth from an inlet adjacent the top of said thermal sink to a point adjacent the bottom thereof and thence upwardly to an outlet adjacent the top thereof.

The invention also comprises one or more further features in which said thermal sink comprises a block of a heat-conductive material having said conduit formed integrally therewith; in which said conduit is routed in said block and covered by a cover plate; in which said conduit has a drain located at the bottom thereof; in which said thermal sink comprises a projection having a cross section complementary with said cold face and in heat-transfer, surface-to-surface contact therewith; in which said thermal sink comprises two parts, one of which comprises said projection and the other one of which comprises a planar surface which includes the flat inner surface of said thermal sink, said projection having a planar surface abutting the planar surface of said thermal sink in heattransfer, surface-to-surface contact therewith; in which the portion of said projection which abuts the planar surface of said thermal sink has a larger cross sectional area than that of the cold face of said thermoelectric element; which further comprises faceplates of non-heat-conductive material fastened to the side edges of said heat-radiating device and said thermal sink; in which said heat-radiating device and said thermal sink are maintained pressed against the faces of said thermoelectric device by said faceplates; which further comprises insulating material insulating said thermal sink from said heat-radiating device; and in which the space bounded by said faceplates is filled with insulating material.

The device thus described is of particular advantage in drying gases preliminary to effecting an analysis thereof or some other operation on the gas which would be adversely affected by the presence of uncondensed liquid therein and functions to bring the gas into contact with the thermal sink of the thermoelectric device in a path which zig-zags from an inlet adjacent the top to a point adjacent the bottom and thence upwardly to an outlet adjacent the top. In this way, the condensed liquid accumulates in the bottom and may be withdrawn either continuosly or periodically through a suitable drain opening in the bottom thereof.

BRIEF DESCRIPTION OF THE DRAWINGS

In the drawings:

FIG. 1 is an exploded view;

FIG. 2 is a cross section taken on line 2-2 of FIG. 1;

FIG. 3 is a cross section taken on line 3-3 of FIG. 1; and,

FIG. 4 is a flow diagram of an exhaust gas analyzer incorporating a thermoelectric drying device according to the invention.

DESCRIPTION OF THE PREFERRED EMBODIMENTS

The invention comprises a thermoelectric device 10 having a thermoelectric element 12 having a hot face 14 and a cold face 16, which element is sandwiched between a heat-radiating device 18 and a thermal sink 20.

The heat-radiating device comprises a block 22 of heat-conducting material having a flat inner surface 24 and an outer surface which is provided with vertical fins 26. The surface 24 is planar and is in heat-transfer, surface-to-surface contact with the flat face 14 of the thermoelectric element 12.

The internal thermal sink is composed of a massive block 28 of heat-conducting material generally rectangular in shape and having an inner planar surface 30 apposed to and substantially coextensive in area with the inner flat surface 24 of the heat-radiating device 18. Between these two flat surfaces, 24 and 30, a block 32 is provided for making heat-transfer contact between the cold face 16 and the casting 28. The heat-transfer block 32 has a flat face 34 adapted to contact the planar face 30 in flat, surface-to-surface, heat-transfer contact. It has another flat surface parallel face 35 which is substantially coextensive in area with the cold face 16 and is in flat, surface-to-surface, heat-transfer contact therewith. The member 32 has an enlarged portion 36 in order to provide greater surface-to-surface contact with the planar surface 30.

The block 28 is routed out at 38 to provide a zig-zag channel which begins at the inlet 40, continues down to the lower right hand corner and then upwardly in a leg 42 to outlet 44. Desirably, a drain 46 is provided at the bottom of leg 42. The front of the block is then sealed off with a faceplate 48 to provide a continuous conduit beginning at inlet 40 and ending at the outlet 44.

The various elements of the device are held in operating position by the side plates 50 and 52, which span the heat-radiating device 10 and the thermal sink 20 and are fastened thereto by bolts or other suitable means so as to hold the various elements in the operative position. Desirably, the space between the two inner surfaces of the heat-radiating surface 10 and the thermal sink 20 is filled with insulation 54 which further serves to hold the various elements in operative position and to prevent or minimize heat transfer from the heat-radiating device 10 to the thermal sink 20.

In assembling the device as described above, the heat-radiating device, the thermoelectric device and the two parts of the thermal sink are placed in a press so that the thermoelectric device is under compression in flat, surface-to-surface contact with the heat-radiating device and the thermal sink. While under this compression, the faceplates 50 and 52 are bolted in place and the insulating material 54 is foamed in place.

If desired, however, the block 32 may be bolted to the heat-radiating device 22 in order to place the thermoelectric element in compression between the face 24 of the heat-radiating device and the face of the block 32. Then the block 28 can be bolted to the block 32 in accordance with practices already well known in the art.

Suitable means, not shown, is provided to impress the requisite direct current potential across the hot and cold faces of the thermoelectric element 12. This is not illustrated as it is a well-known practice in the art.

It will be understood that instead of routing out channels in the block 28, suitable tubing can be cast in the block or otherwise formed to provide a zig-zag conduit of the shape described in heat transfer with the thermal sink; also that various other means may be adopted for providing a zig-zag conduit in heat-transfer contact with the thermal sink.

There is thus provided a simple, easily constructed device of relatively small size which can be hooked into analytical equipment wherever it is necessary or desirable to dry gas prior to analyis.

The device is also versatile in that it can be used for cooling liquids or even for condensing condensable gases.

It is to be understood that the invention is not to be limited to the exact details of construction, operation, or exact materials or embodiments shown and described, as various modifications and equivalents will be apparent to one skilled in the art, and the invention is therefore to be limited only by the full scope of the appended claims.

I claim:

1. A thermoelectric device comprising a thermoelectric element having a cold face and a hot face,
   a heat-radiating device in heat-transfer with said hot face and having a flat, inner surface having a substantially greater area than the area of contact with said hot face and a thermal sink in heat-transfer contact with said cold face and comprising a flat, inner surface apposed to the flat, inner surface of said heat-radiating device and having an area substantially coextensive with the area of the flat, inner surface of the heat-radiating device; and
   a conduit in heat-transfer with said thermal sink,
   said conduit zig-zagging back and forth from an inlet adjacent the top of said thermal sink to a point adjacent the bottom thereof and thence upwardly to an outlet adjacent the top thereof.

2. A thermoelectric device of claim 1, in which said thermal sink comprises a block of a heat-conductive material having said conduit formed integrally therewith.

3. A thermoelectric device of claim 2, in which said conduit is routed in said block and covered by a cover plate.

4. A thermoelectric device of claim 1, in which said conduit has a drain located at the bottom thereof.

5. A thermoelectric device of claim 1, in which said thermal sink comprises a projection having a cross section complementary with said cold face and in heat-transfer, surface-to-surface contact therewith.

6. A thermoelectric device of claim 5, in which said thermal sink comprises two parts, one of which comprises said projection and the other one of which comprises a planar surface which includes the flat, inner surface of said thermal sink, said projection having a planar surface abutting the planar surface of said thermal sink in heat-transfer, surface-to-surface contact therewith.

7. A thermoelectric device of claim 6, in which the portion of said projection which abuts the planar surface of said thermal sink has a larger cross sectional area than that of the cold face of said thermoelectric element.

8. A thermoelectric device which further comprises faceplates of non-heat-conductive material fastened to the side edges of said heat-radiating device and said thermal sink.

9. A thermoelectric device of claim 6, which further comprises face-plates of non-heat-conductive material fastened to the side edges of said heat-radiating device and said thermal sink and in which said heat-radiating device and said thermal sink are maintained pressed against the faces of said thermoelectric device by said faceplates.

10. A thermoelectric device of claim 1, which further comprises insulating material insulating said thermal sink from said heat-radiating device.

11. A thermoelectric device of claim 8, in which the space bounded by said faceplates is filled with insulating material.

12. A device for analyzing exhaust gases which comprises a thermoelectric device of claim 1 interposed between the source of the exhaust gases and an analyzer, whereby the exhaust gases are dried before being fed into the analyzer.

* * * * *